United States Patent [19]

Lantz et al.

[11] Patent Number: 4,800,234

[45] Date of Patent: Jan. 24, 1989

[54] SYNTHESIS OF 1,1,2,2-TETRAHYDROPERFLUOROALKANOLS AND THEIR ESTERS

[75] Inventors: André Lantz, Vernaison; Pascal Michaud, La Mulatiere, both of France

[73] Assignee: Societe ATOCHEM, Puteaux, France

[21] Appl. No.: 128,915

[22] Filed: Dec. 4, 1987

[30] Foreign Application Priority Data

Dec. 22, 1986 [FR] France ................. 86 17984

[51] Int. Cl.$^4$ .................................... C07C 31/38
[52] U.S. Cl. ..................................... 568/842
[58] Field of Search ......................... 568/842

[56] References Cited

U.S. PATENT DOCUMENTS 3,239,557 3/1966 Fasick ..................... 568/842
3,714,271 1/1973 Regan ..................... 568/842

FOREIGN PATENT DOCUMENTS 728217 2/1966 Canada ........................... 568/842
0024224 2/1981 European Pat. Off. ......... 568/842
3035641 5/1982 Fed. Rep. of Germany ... 568/842

*Primary Examiner*—Werren B. Lone
*Attorney, Agent, or Firm*—Stevens, Davis, Miller & Mosher

[57] ABSTRACT

The invention relates to the preparation of 1,1,2,2-tetrahydroperfluoroalkanols and their esters.

A 2-(perfluoroalkyl)ethyl iodide is oxidized using peroxomonosulphuric acid or peroxodisulphuric acid in a carboxylic acid or carboxylic acid ester.

4 Claims, No Drawings

SYNTHESIS OF 1,1,2,2-TETRAHYDROPERFLUOROALKANOLS AND THEIR ESTERS

FIELD OF THE INVENTION

The present invention relates to the preparation of 1,1,2,2-tetrahydroperfluoroalkanols ($R_FCH_2CH_2OH$) and their esters by oxidizing the corresponding 1-(perfluoroalkyl)ethyl iodides ($R_FCH_2CH_2I$). The perfluoroalkyl radical $R_F$ may contain from 1 to 20 carbon atoms and may be straight-chain or branched chain.

BACKGROUND OF THE INVENTION

These polyfluorinated alcohols and esters are valuable intermediates for the production of surface-active agents and hydrophobic and oleophobic substances. In particular, they may easily be converted into acrylic or methacrylic esters. The polymerization of these esters optionally with other monomers, gives hydrophobic and oleophobic finishing agents for textile materials, leather, paper or other substrates. Alcohol and ester mixtures may also be converted entirely into alcohols.

Several processes for the preparation of these polyfluorinated alcohols and esters are known. The process described in French Pat. No. 1,380,579, which reacts an iodide $R_FCH_2CH_2I$ with fuming sulphuric acid and then hydrolyzes the sulphate formed. It has the disadvantage of producing large quantities of sulphuric diesters. These diesters are difficult to hydrolyze. The reference is hereby incorporated by reference.

According to the process described in U.S. Pat. No. 3,239,557, it is possible to obtain the esters $R_FCH_2CH_2OCOR$ by reacting an iodide $R_FCH_2CH_2I$ with a salt of a carboxylic acid RCOOH. However, the yields are not very high because variable quantities of the olefin $R_FCH=CH_2$ are formed. The patent is hereby incorporated by reference.

The alcohols $R_FCH_2CH_2OH$ may also be obtained according to the process of French Pat. No. 2,096,179, hereby incorporated by reference, which relates to preparing the nitrates $R_FCH_2CH_2ONO_2$ by reacting the iodides $R_FCH_2CH_2I$ with nitric acid and to hydrogenating these nitrates into alcohol. However, this process had the disadvantage of requiring two reaction stages, the latter of which must be carried out under a high hydrogen pressure.

French Pat. No. 2,180,113, hereby incorporated by reference, describes a process for the production of mixtures of alcohols $R_FCH_2CH_2OH$ and formates $R_FCH_2CH_2OCOH$ by reacting the iodides $R_FCH_2CH_2I$ with dimethylformamide at high temperature in the presence of a small quantity of water. This process has the disadvantage of requiring very harsh reaction conditions and of producing the olefin $R_FCH=CH_2$ as a by-product. This reduces the yield accordingly. Additionally, a good selectivity for alcohol and formate can only be obtained by using very large quantities of dimethylformamide.

More recently, the preparation of these polyfluorinated alcohols and esters by reacting the iodide $R_FCH_2CH_2I$ with a peroxacid $RCO_3H$ which has previously been formed by adding hydrogen peroxide to a carboxylic acid $RCO_2H$ in the presence or otherwise of a small quantity of sulphiric acid has been proposed in European Pat. No. 24,224 and West German Pat. No. 3,035,641. However, under the operating conditions described, this process leads to the production of an olefin by-product $R_FCH=CH_2$ in a significant quantity and/or to a low conversion rate for the iodide $R_FCH_2CH_2I$. The patents are hereby incorporated by reference.

A process which enables these disadvantages to be overcome, that is, the production of the olefin by-product $R_FCH=CH_2$ is prevented and an excellent conversion rate is obtained, has now been discovered.

SUMMARY OF THE INVENTION

The process according to the invention comprises oxidizing a 2-(perfluoroalkyl)ethyl iodide using peroxomonosulphuric acid or peroxodisulphuric acid in a carboxylic acid or an ester of such an acid.

DETAILED DESCRIPTION

Peroxomonosulphuric acid $H_2SO_5$ and peroxodisulphuric acid $H_2S_2O_8$ may be obtained according to different well-known methods (P. PASCAL, Nouveau Traité de Chimie Minérale, Tome XIII, 1494–1510) (New Treatise on Organic Chemistry, Volume XIII). In view of its instability, the peroxomonosulphuric acid is preferably prepared just before use and is quickly added to a solution of 2-(perfluoroalkyl)ethyl iodide in a carboxylic acid or carboxylic acid ester. The peroxodisulphuric acid which is more stable may be used in the solid state or in the form of aqueous solutions.

As carboxylic acids, aliphatic acids which are liquids under the operating conditions are preferably used. These acids which generally contain from 1 to 8 carbon atoms may be straight-chain or branched chain, saturated or unsaturated, and may contain substituents such as, for example, halogen atoms. Acetic acid and propionic acid are particularly useful.

It is also possible to use solid carboxylic acids such as higher aliphatic acids or aromatic acids (for example benzoic acid and its substituted derivatives) by adding a solvent such as an alcohol (for example methanol, ethanol or propanol) or an ester.

As mentioned above, a carboxylic acid ester may be used. This ester is preferably an ester of an aliphatic alcohol containing 1 to 4 carbon atoms, for example ethyl acetate, butyl acetate or ethyl propionate.

The oxidation according to the invention may be carried out at a temperature which may range from $-20°$ to $140°$ C., but which is advantageously between $60°$ and $90°$ C.

According to a preferred embodiment of the invention, the peroxomonosulphuric acid is prepared by adding hydrogen peroxide to sulphuric acid between $-5°$ C. and $40°$ C. The mixture is then quickly added to a solution of 2-(perfluoroalkyl)ethyl iodide in the carboxylic acid or the carboxylic acid ester. From 1 to 30 moles of sulphuric acid (preferably 5 to 15 moles), from 3 to 20 moles of hydrogen peroxide (preferably 5 to 6 moles) and from 1 to 50 moles of carboxylic acid or carboxylic acid ester (preferably 5 to 15 moles) are used all per mole of iodide.

Hydrogen peroxide is advantageously used in the form of aqueous solutions, the $H_2O_2$ concentration of which may vary from approximately 35 to 75% by weight and is preferably between 65 and 75%.

Although it is preferable to use pure or very concentrated (80% by weight or higher) sulphuric acid, it is also possible to use sulphuric acid solutions containing up to 50% by weight of water.

The oxidation reaction is generally very quick and takes place with the release of iodine and/or of iodic acid which can easily be separated from the reaction mixture by filtration. The major portion of iodine may thus be recovered in the form of elementary iodine by treating the iodic acid with a conventional reducing agent such as sodium sulphite.

The fluorinated products may be isolated according to conventional methods, for example by phase separation and washing the organic phase with water. A product which mainly comprises the 2-(perfluoroalkyl)ethyl ester ($R_FC_2H_4OCOR$) is finally obtained. The ester may be saponified to obtain the alcohol $R_FCH_2CH_2OH$ or be converted into another ester, especially into acrylate or methacrylate.

As it has already been pointed out in the above-cited German Pat. No. 3,035,641, working with peracids and hydrogen peroxide involves not-negligible risks of firing and explosion. Consequently, when carrying out the process according to this invention, it is urged to take all the usual security measures against these risks.

EXAMPLES

The following examples in which the percentages refer to percentages by weight, illustrate the invention without limiting it.

EXAMPLE 1

In order to prepare Caro's acid $H_2SO_5$, 50 ml of 98% sulphuric acid are introduced into an Erlenmeyer flask standing in ice and 24.7 g of an aqueous 70% hydrogen peroxide solution (which amounts to 0.5 mole of $H_2O_2$) are then added dropwise in the course of one hour.

The mixture obtained is then added quickly (in 5 to 10 minutes) to a solution of 47.4 g (0.1 mole) of 2-(perfluorohexyl)ethyl iodide $C_6F_{13}C_2H_4I$ in 60 g of acetic acid. The temperature of the reaction mixture rises quickly from 20° C. to 75°–80° C. The latter is maintained for a further period of approximately 45 minutes by heating.

After filtering the reaction mixture in order to remove the iodic acid formed, phase separation of the filtrate is carried out. The organic phase is washed with 3×50 ml of water at 25° C. 38 g of organic phase are thus obtained. The chromatographic analysis of which shows the following distribution of fluorinated compounds:
- 94.8% of $C_6F_{13}C_2H_4OCOCH_3$,
- 1.9% of $C_6F_{13}C_2H_4OH$,
- 3% of $(C_6F_{13}C_2H_4O)_2SO_2$, and
- 0.3% of unconverted $C_6F_{13}C_2H_4I$.

EXAMPLE 2

Operating as in Example 1, starting with 57.4 g (0.1 mole) of 2-(perfluorooctyl)ethyl iodide $C_8F_{17}C_2H_4I$, 43 g of organic phase are obtained. The distribution of fluorinated compounds in the organic phase is as follows:
- 92% of $C_8F_{17}C_2H_4OCOCH_3$,
- 1.8% of $C_8F_{17}C_2H_4OH$,
- 3.1% of $(C_8F_{17}C_2H_4O)_2SO_2$, and
- 3.1% of unconverted $C_8F_{17}C_2H_4I$.

EXAMPLE 3

The reaction is carried out as in Example 1, but the 2-(perfluorohexyl)ethyl iodide is replaced by 53.8 g of a mixture of iodides $R_FC_2H_4I$ having the following composition by weight:

| $R_F$ | % |
|---|---|
| $C_6F_{13}$ | 56.1 |
| $C_8F_{17}$ | 25.0 |
| $C_{10}F_{21}$ | 10.1 |
| $C_{12}F_{25}$ | 4.0 |
| $\geq C_{14}F_{29}$ | 4.8 |

The average molecular weight of this mixture is approximately 538.

The distribution of fluorinated compounds in the organic phase thus obtained (40 g) is as follows:
- 80% of $R_FC_2H_4OCOCH_3$,
- 4.5% of $R_FC_2H_4OH$,
- 14.7% of $(R_FC_2H_4O)_2SO_2$, and
- 0.8% of unconverted $R_FC_2H_4I$.

EXAMPLE 4

15 ml of 98% sulphuric acid are introduced into a beaker which is cooled by an ice-cold water bath. 10 g of potassium persulphate are then introduced during an approximately 15 minute period. After diluting the mixture with an equal volume of water, it is quickly added to a solution of 4.7 g of 2-(perfluorohexyl)ethyl iodide in 10 ml of acetic acid. The mixture is allowed to react for 2 hours.

After phase separation, chromatographic analysis of the organic phase (4 g) shows the following distribution of fluorinated compounds:
- 90% of $C_6F_{13}C_2H_4OCOCH_3$
- 7% of $C_6F_{13}C_2H_4OH$, and
- 3% of unconverted $C_6F_{13}C_2H_4I$.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for the preparation of 1,1,2,2-tetrahydroperfluoroalkanols and their esters, comprising oxidizing a 2-(perfluoroalkyl)ethyl iodide using peroxomonosulphuric acid or peroxodisulphuric acid in a carboxylic acid or an ester of such an acid.

2. The process according to claim 1, further comprising carrying out the reaction at a temperature of between 60° and 90° C.

3. The process according to claim 1, further comprising preparing the peroxomonosulphuric acid by adding hydrogen peroxide to sulphuric acid and adding this mixture to a solution of 2-(perfluoroalkyl)ethyl iodide in the carboxylic acid or the carboxylic acid ester.

4. The process according to claim 3, further comprising using from 1 to 30 moles of sulphuric acid, from 3 to 20 moles of hydrogen peroxide and from 1 to 50 moles of carboxylic acid or carboxylic acid ester, all per mole of 2-(perfluoroalkyl)ethyl iodide.

* * * * *